United States Patent [19]

Ooms et al.

[11] Patent Number: 5,710,310
[45] Date of Patent: Jan. 20, 1998

[54] PROCESS FOR THE CONTINUOUS PRODUCTION OF DIARYL CARBONATES

[75] Inventors: Pieter Ooms; Hans-Josef Buysch, both of Krefeld; Steffen Kühling, Meerbusch; Gottfried Zaby, Leverkusen, all of Germany

[73] Assignee: Bayer Aktiengesellschaft

[21] Appl. No.: 690,332

[22] Filed: Jul. 25, 1996

[30] Foreign Application Priority Data

Aug. 2, 1995 [DE] Germany ............ 195 28 298.1

[51] Int. Cl.⁶ .................................................. C07C 69/96
[52] U.S. Cl. ................................. 558/274; 558/270
[58] Field of Search ................................. 558/274

[56] References Cited

U.S. PATENT DOCUMENTS

| | | | |
|---|---|---|---|
| 2,362,865 | 11/1944 | Tyron et al. | 260/463 |
| 2,837,555 | 6/1958 | Lee | 260/463 |
| 3,234,263 | 2/1966 | Kurkjy et al. | 260/463 |
| 5,478,961 | 12/1995 | Ooms et al. | 558/274 |
| 5,527,942 | 6/1996 | Ooms et al. | 558/274 |

FOREIGN PATENT DOCUMENTS

| | | |
|---|---|---|
| 516 355 A2 | 12/1992 | European Pat. Off. . |
| A 0 483 632 | 5/1992 | Germany . |
| A 0 635 476 | 1/1995 | Germany . |
| A 0 645 364 | 3/1995 | Germany . |
| WO 91/06526 | 5/1991 | WIPO . |

*Primary Examiner*—Raymond Henley, III
*Assistant Examiner*—Dwayne C. Jones
*Attorney, Agent, or Firm*—Connolly & Hutz

[57] ABSTRACT

The present invention relates to a process for the continuous production of diaryl carbonates by reaction of aromatic hydroxy compounds with phosgene in the presence of heterogeneous catalysts.

2 Claims, 1 Drawing Sheet

PROCESS FOR THE CONTINUOUS PRODUCTION OF DIARYL CARBONATES

BACKGROUND OF THE INVENTION

The present invention relates to a process for the continuous production of diaryl carbonates by reaction of aromatic hydroxy compounds with phosgene in the presence of heterogeneous catalysts.

It is known that aryl carbonates can be obtained by phase-interface phosgenation (Schotten-Baumann reaction) of aromatic hydroxy compounds. In this process the use of solvents and caustic soda solution has a disadvantageous effect, since by virtue of the aqueous alkaline solution a partial saponification of phosgene or chlorocarbonic ester can take place, large quantities of common salt accumulate as by-product and the solvent has to be recovered.

Proposals for processes without solvent are to be found, for instance, in U.S Pat. Nos. 2,837,555; 3,234,263; 2,362, 865. But soluble catalysts are employed, the separation of which from the products is elaborate.

Consequently it seems sensible to make use of heterogeneous, insoluble catalysts, which substantially facilitate processing of the reaction mixture. Suggestions to this end have also been made. For instance, in EP-A 516 355 aluminum trifluoride, which is optionally applied onto supports such as aluminosilicates, is especially recommended. However, the synthesis of aluminium fluoride is very elaborate and more costly, owing to the handling of fluorine or hydrofluoric acid. Furthermore, in WO 91/06526 metal salts on porous supports are described as catalysts for the reactions according to the invention. Fully continuous phosgenation of phenol on such catalysts is possible only in the gas phase, but this entails relatively high reaction temperatures and the risk of decomposition of the sensitive chloroformates. Phosgenation of phenol with these catalysts in the liquid phase is apparently not feasible, since the hot, liquid phenol washes out the active catalyst components.

Accordingly no proposal has been made hitherto with regard to achieving a continuous procedure for the production of diaryl carbonates by phosgenation of aromatic hydroxy compounds in the presence of heterogeneous catalysts.

SUMMARY AND DETAILED DESCRIPTION OF THE INVENTION

Such a process has now been found. It is characterized in that 1) a mixture consisting of aromatic hydroxy compound and optionally the chloroformates thereof is introduced together with phosgene into a reactor that is filled with heterogeneous catalyst and is caused to be reacted therein in such a way that the heat of reaction is dissipated by evaporation of the educts and products and thus the reaction temperature increases by a maximum of 50° C. above the admission temperature of the reaction mixture, 2) the product leaving the reactor is degassed, the waste gas is sent towards a flow of the molten aromatic hydroxy compound which optionally contains some chloroformate, whereby phosgene, aromatic hydroxy compound and the chloroformates thereof are removed from the flow of waste gas, 3) the reaction product that has been withdrawn from the reactor and degassed is either supplied directly for processing or is fed into a second reactor in which residual chloroformate is caused to react further, over heterogeneous catalyst, with aromatic hydroxy compound that is still present or that has been fed in so as to form diaryl carbonate, 4) the product leaving the second reactor is in turn degassed and this waste gas is supplied for the washing with molten aromatic hydroxy compound specified under 2), 5) the degassed product is fed from the second reactor into a distillation column, aromatic hydroxy compound and, where appropriate, traces of chloroformate which may still be present are distilled off via the head and introduced again into the first reactor, 6) the sump of this first column is supplied to a second distillation column, traces of low-boiling components which may, where appropriate, still be present in it are removed from the diaryl carbonate via the head, said traces being returned into the upper part of the first column, 7) pure diaryl carbonate is discharged from the gas space of the second column, 8) the sump of this second column is supplied to a third distillation unit, diaryl carbonate is distilled off via the head, is returned into the second column, and the high-boiling components are withdrawn from the sump of the third distillation unit.

Aromatic hydroxy compounds for the process according to the invention are those of the formula ArOH, wherein Ar signifies phenyl, naphthyl, anthryl, phenanthryl, indanyl, tetrahydronaphthyl or the residue of a 5- or 6-membered aromatic heterocycle with 1 or 2 heteroatoms selected from the group comprising N, O and S, whereby these isocyclic and heterocyclic residues may be substituted by one or more substituents such as straight-chained or branched $C_1$–$C_4$-alkyl, $C_1$–$C_4$-alkenyl, $C_1$–$C_4$-alkoxy groups, phenyl residues or nitrile and halogen functions, and whereby furthermore the heterocyclic residues may be fused to a benzene nucleus.

Examples of aromatic hydroxy compounds according to the invention are: phenol, o-, m- and p-cresol, o- m- and p-isopropylphenol, the corresponding halogen or alkoxy phenols such as p-chlorophenol or p-methoxyphenol, furthermore monohydroxy compounds of naphthalene, anthracene and phenanthrene, furthermore 4-hydroxypyridine and hydroxyquinoline. Use is preferably made of substituted phenols, phenol itself being particularly preferred.

Suitable catalysts for the process according to the invention are known in principle, for instance from EP-A 483 632, EP-A 635 476, U.S. Pat. No. 5,478,961, EP-A 635 477, U.S. Pat. No. 5,473,094, EP-A 645 364, EP-A 691 326, EP-A 516 355, U.S. Pat. Nos. 5,239,105 and 5,136,077.

The educts phosgene and hydroxy compound are employed in molar ratios of 1:0.5 to 1:8, preferably 1:1.5 to 1:5, and particularly preferably 1:2 to 1:4. The stoichiometric ratio in this case is 1:2.

The catalysts are used, as a rule, as granular material, granulates, extradates, rods, balls, moulded bodies having a large surface area such as hollow extrudates in the form of Raschig rings, hollow cylinders, stars, waggon wheels, or as fragments. The diameter and length of these particles amount to 0.5 to 10 mm. They are arranged in the reactor in the form of simple heaps.

Suitable reactors for the process according to the invention are known to those skilled in the art. Examples are tubular reactors, optionally with a cooling or heating jacket, which contain the catalyst in the form of a heap, or shelf-type reactors in which the catalyst is distributed in the form of a uniform layer onto several plates located above one another.

To cause reaction, phosgene and aromatic hydroxy compound may be conducted through the reactor in concurrent flow or in counterflow. In the case of reactors that stand vertically the liquid phase can be conducted through the reactor both downwards from above and upwards from below.

The reaction of phosgene and aromatic hydroxy compound is carried out at temperatures of about 100° to 250° C., preferably 120° to 230° C., and particularly preferably 130° to 220° C. The heat of reaction is dissipated by evaporation of educts and products to such an extent that the temperature of the reaction mixture increases by a maximum of 50° C., preferably at most 40° C., and particularly preferably no more than 35° C., above the admission temperature of the reactants.

The pressure ranges between 0.3 and 10 bar, preferably 0.5 and 7 bar, and particularly preferably 0.8 and 6 bar.

The waste gas formed in the course of the reaction is cooled and in a counterflow apparatus is sent towards a molten flow of the hydroxy compound, which may also contain chloroformate in quantities from <50 wt-%, preferably <30 wt-%, and particularly preferably <10 wt-%, whereby residual phosgene and, where appropriate, smaller quantities of hydroxy compounds and chloroformate that are still entrained are withdrawn from the gas flow. The liquid mixture leaving the counterflow apparatus is adjusted to the desired molar ratio by addition of phosgene and, optionally, further hydroxy compound, heated to the desired temperature and supplied to the reactor.

The counterflow apparatus may be, for example, a packed column, a plate-type column with sieve plate, a bubble-column cascade or a cascaded bubble column which contains in a vertical pipe several bubble columns arranged above one another and connected to one another via the gas space and overflow pipes or weirs.

The gas flow emerging at the head of the counterflow apparatus consists substantially of hydrogen chloride. Traces of phosgene which may still be present may be hydrolysed in accordance with known methods in an activated-carbon tower with a little water. The quantity of hydroxy compound that is still present in the flow of hydrogen chloride in accordance with its vapour pressure at the temperature prevailing in the counterflow apparatus is expelled in the form of an aqueous mixture in the subsequent adiabatic absorption of the hydrogen chloride in water by azeotropic distillation and may, after recovery, be supplied to the reactor or used for other purposes, such as the production of phenol resins.

The residual quantities of phosgene that are still present in the hydrogen chloride may also, after the adiabatic absorption with water when they are expelled with the azeotrope consisting of hydroxy compound and water, be supplied advantageously to the activated-carbon tower together with the residual traces of inert gas originating from the flows of educt and may be hydrolysed in said tower.

After the degassing of the reaction mixture a first raw product is obtained which as a role consists predominantly of diaryl carbonate and/or aromatic hydroxy compound and which still contains certain quantities of chloroformate which amount as a rule to <50 wt-%, preferably <30 wt-%, and particularly preferably <15 wt-%.

This mixture can be supplied directly for processing by distillation and divided up into flows consisting of chloroformate and hydroxy compound, a diaryl carbonate and small quantities of high-boiling components. However, use of a reaction mixture that contains no chloroformate or only small quantities thereof will lead to simplification and more economic implementation of the distillation.

Therefore the first raw product that is obtained after the degassing is advantageously conducted into a second reactor containing heterogeneous catalyst, and the chloroformate that is still present is caused to react therein with hydroxy compound that is still present in the mixture or that is added, under similar conditions as in the first reactor. In this process the pressure may lie within narrower limits of 0.6 to 6, preferably 0.8 to 4 bar, and the temperature may be somewhat higher, namely from 120° to 250° C., preferably 140° to 240° C., and particularly preferably 160° to 230° C.

The loading of the reactors, measured in kilograms of educt mixture per liter of catalyst volume per hour, depends on the reaction temperature, the activity of the catalysts and the desired conversion. It amounts to 0.01 to 20, preferably 0.02 to 10, particularly preferably 0.05 to 4, and most particularly 0.1 to 3 kg/l.h.

The mixture leaving the second reactor is also degassed, the flow of waste gas is also conducted into the counterflow apparatus and washed. The degassed mixture, which contains only small quantities (<3, preferably <2, and particularly preferably <1 wt-%) of chloroformate, is freed in a first distillation column from excess hydroxy compound and chloroformate, which are removed as head product and, as required, conducted into the first or second reactor and caused to react further.

The mixture that drains off at the base of this column is separated in a second column into residual low-boiling components, which are returned into the upper part of the first column, pure diaryl carbonate, which is withdrawn laterally from the vapour flow of this second column, and a mixture consisting of diaryl carbonate and high-boiling components, which leaves the column in the form of sump.

This sump is separated in a third distillation device, which is operated continuously or discontinuously, into a sump that contains the high-boiling components and into diaryl carbonate that is conducted into the lower part of the second column and purified further therein.

The comparatively small quantities of sump of <3, preferably <2, and particularly preferably <1%, of the reaction product are expediently incinerated or used for the production of phenol resin.

EXAMPLE 1

Figure 1:
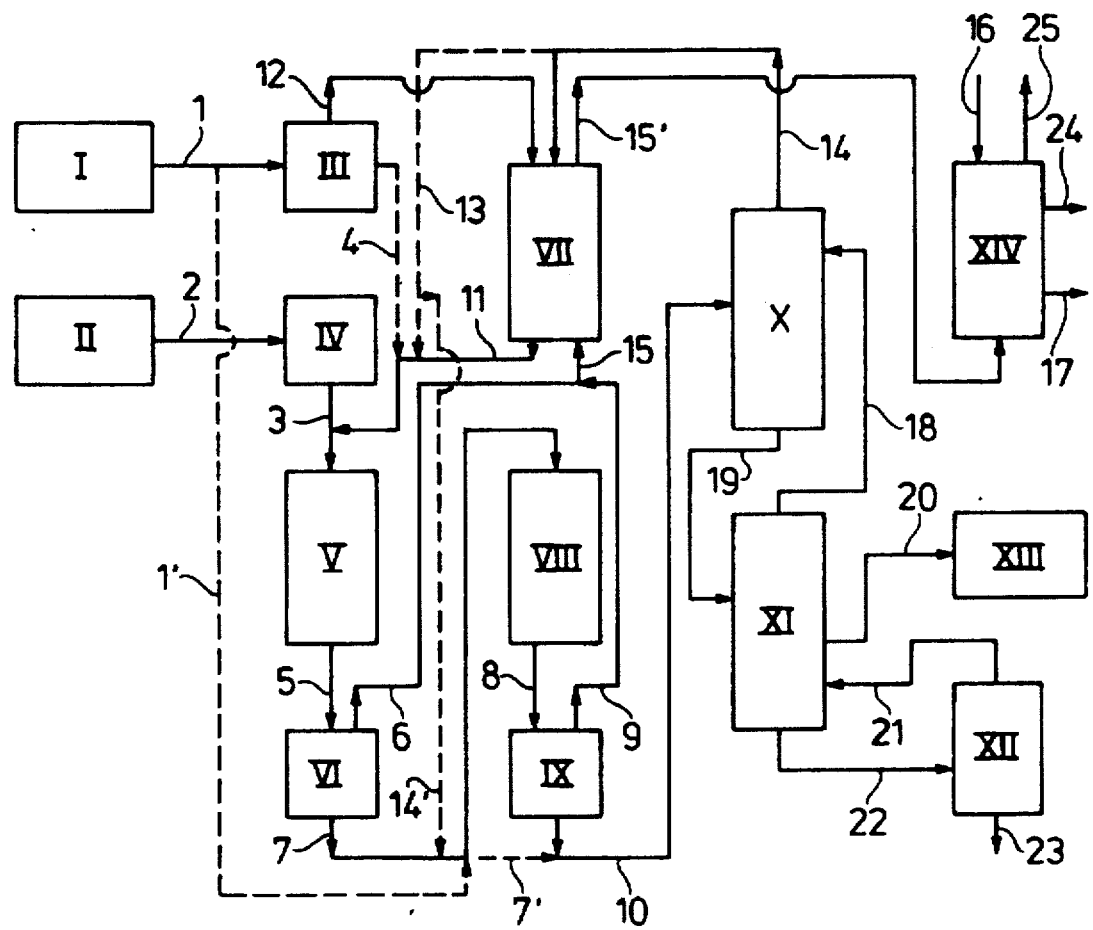
FIG. 1 shows a schematic illustration of the apparatus employed in the present invention.

Continuous Production of Diphenyl Carbonate by Phosgenation of Phenol in the Presence of γ-aluminum Oxide The apparatus that is used for implementing the process according to the invention and the flows of material arising are reproduced schematically in FIG. 1.

From a heated storage container I, 41.12 wt-parts/h of phenol 1 are dosed from above via heat exchanger III (60° C.) under normal pressure into a counterflow column VII heated to 60° C. and charged with fillers in which mixing with phenol 14 withdrawn from the distillation column X at the head takes place. After the flow 15 of waste gas originating from the degassing apparatus VI and IX has passed through VII, mixture 11 (weight ratio of phenol to phosgene about 97/3) is fed out at the base. 21.93 wt-parts/h of preheated phosgene 3 are introduced in concurrent flow via heat exchanger IV (170° C.) together with 11 into a reactor V heated to 170° C. and filled with 150 parts by volume of γ-aluminum oxide.

The product 5 emerging at the base of the reactor, which contains phenol, phenyl chloroformate, diphenyl carbonate and by-products in a ratio of 56.1/0.8/42.8/0.3, is separated via degasser VI into waste gas 6 (weight ratio of phenol, phosgene, hydrogen chloride and carbon dioxide 2.5/15.8/81.1/0.6) and sump 7 (weight ratio of phenol, phenyl chloroformate, diphenyl carbonate and by-products 55.8/0.9/43.0/0.3).

The phenyl chloroformate present in the sump 7 is caused to react by post-reaction with existing phenol (possibly after addition of additional phenol 1' or 14') in a second reactor VIII, also filled with γ-aluminium oxide (150 parts by volume) at 180° C. so as to form diphenyl carbonate.

The product 8 withdrawn at the base of the reactor (weight ratio of phenol, diphenyl carbonate and by-products 55.4/44.3/0.3) is separated via degasser IX into waste gas 9 (phenol and hydrogen chloride) and sump 10 (weight ratio of phenol, diphenyl carbonate and by-products 55.2/44.5/0.3).

Flows 6 and 9 of waste gas are combined to form 15 (weight ratio of phenol, hydrogen chloride and carbon dioxide 5.8/93.6/0.6) and conducted through phenol in the counterflow apparatus VII.

The waste gas 15' emerging at the head is supplied to a unit for absorption of hydrogen chloride XIV.

By feeding in 94.3 wt-parts/h of an 18% solution of hydrochloric acid 16, 110.5 wt-parts/h of a 30% solution of hydrochloric acid 17 are obtained, which can be supplied for electrolysis. The chlorine obtained from the electrolysis can be used again for the production of phosgene.

Traces of entrained phenol may be removed as azeotrope with water 24.

To effect the decomposition of phosgene that is still present in traces in the waste gas 25 an annihilation unit (activated-carbon towers with water) is connected.

Sump 10 is fed into a first distillation column X and separated at about 80° C./12 mm into 57.7 wt-parts/h phenol and sump 19 (weight ratio of phenol, diphenyl carbonate and by-products 0.3/99.1/0.6).

Sump 19 is conducted into a second distillation column XI in which phenol that is still present (0.14 parts by weight) is removed via the head and is returned into the upper part of the first column X. The product 22 withdrawn at the base (weight ratio of diphenyl carbonate to by-products 88.6/11.4) is separated in a third distillation column XII at 170° C./12 mm into head product 21 (2.3 wt-parts/h diphenyl carbonate), which is returned into the lower part of the second column XI, and sump 23 (high-boiling by-products).

By lateral discharge from the gas space of the second column XI 46.6 wt-parts/h of product 20 (weight ratio of diphenyl carbonate, phenol 99.8/0.2) are obtained.

EXAMPLE 2

The process is conducted as described in example 1, but without the counterflow apparatus VII. By feeding into reactor V 32.0 wt-parts/h of phenol 12 via heat exchanger III and 10.7 wt-parts/h of phosgene 3 via heat exchanger IV, 20.1 wt.parts/h of diphenyl carbonate are obtained with constant selectivity.

EXAMPLE 3

The process is conducted as described in example 2. By feeding into reactor V 30.0 wt.-parts/h of phenol 12 via heat exchanger III and 15.0 wt.-parts/h of phosgene 3 via heat exchanger IV, 24.3 wt.-parts/h of diphenyl carbonate are obtained with constant selectivity.

By way of further variations in the described procedure, depending on the compositions of educt and product, catalyst loads and temperature, the following may be mentioned:

a) Dosing of phenol 4 directly into reactor V instead of via counterflow apparatus VII when starting up or in the case of a mode of operation without counterflow apparatus.

b) Addition of phenol (1' or 14') by way of additional reaction partner for the post-reaction in the case where relatively large concentrations of phenyl chloroformate are present.

c) Mode of operation without post-reaction in the second reactor VIII, whereby phenyl chloroformate that is still present is then distilled off in the first distillation column X as low-boiling component 14 with phenol and is fed into counterflow apparatus VII, or, in the case of a mode of operation without counterflow apparatus, is returned (13) into the first reactor V.

d) Liquid phase and phosgene are conducted through reactor V in counterflow. In this process phosgene from the storage container 11 enters the reactor V from below via heat exchanger IV, and the liquid phase enters from above. With a view to carrying away the waste gas formed, the upper part of the reactor V is additionally connected to counterflow column VII.

e) Residual phenol contained in waste gas 15' is removed in a condenser and returned to counterflow apparatus VII, first reactor V, or second reactor VIII.

e) Diaryl carbonate 20 is purified in a fourth distillation unit, whereby pure diaryl carbonate is distilled off via the head and residual high-boiling components are returned to the third distillation unit XII together with sump 22 from the second distillation column XI.

We claim:

1. Process for continuous production of diaryl carbonates by reaction of phosgene with aromatic hydroxy compounds in the presence of heterogeneous catalysts, comprising the steps of (1) introducing a reaction mixture consisting of aromatic hydroxy compound and optionally chloroformates thereof together with phosgene into a reactor filled with heterogeneous catalyst and reacting the mixture in such a way that heat of reaction is dissipated by evaporation of educts and products and whereby reaction temperature increases by a maximum of 50° C. above admission temperature of the reaction mixture, (2) degassing product leaving the reactor, sending waste gas towards a flow of molten aromatic hydroxy compound which optionally contains some chloroformate, whereby phosgene, aromatic hydroxy compound and the chloroformate thereof are removed from the flow of waste gas, (3) feeding reaction product withdrawn from the reactor and degassed into a second reactor in which residual chloroformate is caused to react further, over heterogeneous catalyst, with aromatic hydroxy compound still present or that has been fed in so as to form diaryl carbonate, (4) degassing product leaving the second reactor, supplying waste gas for washing with molten aromatic hydroxy compound specified under step (2), (5) feeding degassed product from the second reactor into a distillation column to distill off aromatic hydroxy compound and, where appropriate, chloroformate still present and introducing distilled product from the distillation column into the first reactor, (6) supplying sump of this first column to a second distillation column, whereby traces of low-boiling components which may, where appropriate, still be present in it are removed from the diaryl carbonate, and returning the traces into an upper part of the first column, (7) discharging diaryl carbonate from a gas space of the second column, and (8) supplying sump of the second column to a third distillation unit, whereby diaryl carbonate is distilled off and returned into the second column, and high-boiling components are withdrawn from a sump of the third distillation unit.

2. Process for continuous production of diaryl carbonates by reaction of phosgene with aromatic hydroxy compounds in the presence of heterogeneous catalysts, comprising the steps of (1) introducing a reaction mixture consisting of aromatic hydroxy compound and optionally chloroformates thereof together with phosgene into a reactor filled with heterogeneous catalyst and reacting the mixture in such a way that heat of reaction is dissipated by evaporation of educts and products and reaction temperature increases by a maximum of 50° C. above admission temperature of the reaction mixture, (2) degassing product leaving the reactor, sending waste gas towards a flow of molten aromatic hydroxy compound which optionally contains some chloroformate, whereby phosgene, aromatic hydroxy compound and the chloroformate thereof are removed from the waste gas, (3) feeding degassed reaction product withdrawn from the reactor into a distillation column to distill off aromatic hydroxy compound and, where appropriate, chloroformate still present and introducing distilled product from the distillation column into the reactor, (4) supplying sump of this first column to a second distillation column, whereby traces of low-boiling components which may, where appropriate, still be present in it are removed from the diaryl carbonate, and returning the traces into an upper part of the first column, (5) discharging diaryl carbonate from a gas space of the second column, and (6) supplying sump of the second column to a third distillation unit, whereby diaryl carbonate is distilled off and returned into the second column, and high-boiling components are withdrawn from a sump of the third distillation unit.

* * * * *